US006660882B2

(12) United States Patent
Barve et al.

(10) Patent No.: US 6,660,882 B2
(45) Date of Patent: Dec. 9, 2003

(54) PROCESS FOR THE PREPARATION OF 2-METHYL-2-PROPENE-1-SULFONIC ACID, SODIUM SALT

(75) Inventors: Prashant Purushottam Barve, Maharashtra (IN); Sunil Shankar Joshi, Maharashtra (IN); Ravindra William Shinde, Maharashtra (IN); Shrikant Madhukar Ghike, Maharashtra (IN); Milind Yashwant Gupte, Maharashtra (IN); Chandrashekhar Narayan Joshi, Maharashtra (IN); Raghavendra Venkatrao Naik, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/098,525

(22) Filed: Mar. 18, 2002

(65) Prior Publication Data

US 2003/0176731 A1 Sep. 18, 2003

(51) Int. Cl.$^7$ .............................................. C07C 309/00
(52) U.S. Cl. ........................................ 562/123; 562/115
(58) Field of Search ........................... 562/30, 115, 120, 562/123, 124

(56) References Cited

U.S. PATENT DOCUMENTS

| 1,498,168 A | * | 6/1924 | Hill .............................. 423/532 |
| 2,807,642 A | * | 9/1957 | Bloch et al. ................... 562/96 |
| 3,694,493 A | * | 9/1972 | Lorenz et al. ............... 562/123 |
| 3,794,211 A | * | 2/1974 | Okumura et al. ........... 220/89.2 |
| 4,026,926 A | * | 5/1977 | Takata et al. ............... 562/123 |

* cited by examiner

Primary Examiner—Jean F. Vollano
(74) Attorney, Agent, or Firm—Burns, Doane, Swecker & Mathis, L.L.P.

(57) ABSTRACT

The present invention provides a process for the preparation of highly pure 2-Methyl-2-propene-1-sulfonic acid, sodium salt in high yield, with very low iron content, by the reaction of distilled sulfur trioxide complexed with a Lewis base in a halogentated solvent, the unreacted sulfur trioxide vapors being removed from the reactor before the mixture is treated with liquefied isobutylene, and neutralization by a base with an iron content within the range of 0 to 20 ppm.

17 Claims, No Drawings

PROCESS FOR THE PREPARATION OF 2-METHYL-2-PROPENE-1-SULFONIC ACID, SODIUM SALT

FIELD OF THE INVENTION

The present invention relates to a process for preparation of highly pure 2-Methyl-2-propene-1-sulfonic acid, sodium salt. More particularly the present invention relates to a process for the preparation of highly pure 2-Methyl-2-propene-1-sulfonic acid, sodium salt in high yield, with very low iron content, by the reaction of distilled sulfur trioxide complexed with a Lewis base in a halogentated solvent, removing the unreacted sulfur trioxide vapors from the reactor before the mixture is treated with liquefied isobutylene, and neutralization by a base iron content within the range of 0 to 20 ppm.

BACKGROUND OF THE INVENTION

2-Methyl-2-propene-1-sulfonic acid, sodium salt as well as its homologues are used for improving the affinity of the acrylic fibers, towards dyes, in the dyeing process. 2-Methyl-2-propene-1-sylfonic acid, sodium salt and its homologues function as co-monomers during the polymerization process with acrylic monomers. Further, the homopolymers or the co-polymers of 2-Methyl-2-propene-1-sulfonic acid, sodium salt as well as its homologues, are used as extremely superior high molecular electrolytes, brighteners for electroplating, lubricating anti wear and $H_2S$ neutralizing additive for water based drilling mud. However, highly pure material is required (with the aim of obtaining the water soluble polymer that is colorless, has high molecular weight and high solubility). The iron content in the product must not exceed 3 ppm.

The manufacturing method for 2-Methyl-2-propene-1-sulfonic acid, sodium salt known in the art consists, in general, of preparing a complex of $SO_3$ with solvents like dimethylformamide, dimethylacetamide, tetra alkyl urea or dioxane in an inert solvent like ethylene dichloride or methylene chloride or n-methyl pyrrolidone etc., reacting this complex with isobutylene followed by neutralization with aqueous sodium hydroxide etc. Another method of manufacturing 2-Methyl-2-propene-1-sulfonic acid, sodium salt known in the art is based on reaction of sodium sulfite with allyl chloride or methallyl chloride. Various methods of manufacturing 2-Methyl-2-propene-1-sulfonic acid, sodium salt based on the above general methods have been suggested in the prior art.

Reference is made to Patents Ger. Offen. 1804135 (dated Apr. 30, 1970) Ger. East 70086 (dated Dec. 5, 1969) and Japan 76 56792 (dated May 18, 1976) for the manufacture of 2-Methyl-2-propene-1-sulfonic acid, sodium salt which described a process of manufacture, using allyl chloride or methyl chloride and sodium sulfite as reacting components.

However, this method unavoidably leads to the formation of large amounts of inorganic salts like sodium chloride, sodium sulfate and sodium sulfite. Therefore, these processes need very complex methods of isolation and refinement of the desired product. Similarly, the large quantity of effluent needs to be treated before disposal. Hence, the process may become uneconomical.

Reference is also made to the method based on sulfur trioxide-dioxane complex disclosed in J. Am. Chem. Soc. Vol. 63, Page 978, 1941 and subsequent patents Japan 73 34827 (dated May 25, 1973), Japan 73 56621 (dated Aug. 9, 1973), Japan 76 43715 (dated Apr. 14, 1976), and JP 57007145 B4, (dated Feb. 9, 1982). These references disclose improvements over the base method of $SO_3$-dioxane route. Although this route in general improves the yield of the desired 2-Methyl-2-propene-1-sulfonic acid, sodium salt, they also produce comparatively large quantities of side products. Furthermore the complex of $SO_3$-dioxane is extremely unstable and has to be maintained under controlled conditions. Therefore this route of manufacture is also not very practicable.

A review of the latest developments in sulfonation with complex systems consisting in general of, preparing a complex of $SO_3$ with a Lewis base like dimethylformamide or dimethylacetamide, reveal some reports for preparation of 2-Methyl-2-propene-1-sulfonic acid, sodium salt by sulfonation of isobutylene with $SO_3$-Lewis base complex. Reference is made to Patents Ger. Offen. 1804833 (dated Jul. 9, 1970), Ger. Offen. 1965002 (dated Jul. 1, 1971), Japan Kokai 74 43926 (dated Apr. 25, 1974). And Japan JP 63088167 A2, (dated Apr. 19, 1988), in which the method of preparation of 2-Methyl-2-propene-1-sulfonic acid, sodium salt is in general described. In these dislcosures, isobutylene is sulfonated by the above mentioned complex of $SO_3$ with dimethylformamide or dimethylacetamide in an inert solvent like ethylene dichloride or methylene chloride etc. followed by neutralization with aqueous sodium hydroxide. Similarly the patent Japan Kokai 75 123625 (dated Sep. 29, 1975) also describes a method of isolation of the product from the by product sulfate salts by treating the solution with a lower aliphatic alcohol like methanol and concentration or drying to get the pure product.

However, it is observed that during the process of mixing of isobutylene with $SO_3$-Lewis base complex, a black material is generated which contaminates the product later. Furthermore, it is also observed that the formation of the black coloured contaminant was due to the vapor phase sulfonation of isobutylene at uncontrolled rate in the vapor space of the reactor resulting in the formation of tar. The formation of black coloured contaminant occurs even when product the product is isolated using methanol for precipitation. While in this method, the byproduct sulfone compounds or sodium sulfate etc. can be removed to a large extent, still the coloration takes place and the product appears off-while and the product does not meet the specifications on color which should be less than 10 APHA for 5% aqueous solution.

Extensive research and analysis on the phenomenon of coloration and black material formation during the reaction show that the cause of coloration in final product was specifically due to iron contained in the 2-Methyl-2-propene-1-sulfonic acid, sodium salt as an impurity. They present invention provides the solution to the above mentioned disadvantages of the past methods.

OBJECTS OF THE INVENTION

The main object of the present invention is to provide an improved method for the preparation of highly pure 2-Methyl-2-propene-1-sulfonic acid, sodium salt in high yield, with very low iron content.

Another object of the present invention is to eliminate the formation of black material during the course of addition of isobutylene in the $SO_3$-Lewis base complex in the preparation of highly pure 2-Methyl-2-propene-1-sulfonic acid, sodium salt.

Still another object of the present invention is to reduce the iron content in the final product, thereby improving the color.

Another object of the invention is to provide a process for the preparation of highly pure-2-Methyl-2-propene-1-sulfonic acid, sodium salt with very low iron content, which obviates the disadvantages of the past methods.

SUMMARY OF THE INVENTION

Accordingly the present invention provides a process for the preparation of highly pure 2-Methyl-2-propene-1-sulfonic acid, sodium salt in high yield and with very low iron content comprising reacting distilled sulfur trioxide complexed with a Lewis base, in a halogenated solvent, removing unreacted $SO_3$ vapors, treating the mixture with liquefied isobutylene, neutralizing the reaction mixture with a base, separating the layers into a heavy organic and a lighter aqueous layer, separating the impurities from the aqueous layer by precipitation in a non-solvent, removing the solvent to obtain the product.

In one embodiment of the invention, the distilled sulfur trioxide is substantially free from iron.

In another embodiment of the invention, the Lewis base is selected from dimethylformamide and dimethylacetamide.

In another embodiment of the invention the molar ratio of the Lewis base with distilled $SO_3$ is in the range of 1.5:1 to 2.5:1, preferably 2:1.

In still another embodiment, the molar ratio of isobutylene to distilled $SO_3$ is in the range of 1:1 to 1.3:1, preferably 1.15:1

In another embodiment of the invention, the halogenated solvent is selected from ethylene dichloride and methylene chloride.

In yet another embodiment of the invention, the molar ratio of halogenated solvent to the distilled $SO_3$ is in the range of 5:1 to 9:1 preferably 7:1.

In another embodiment of the invention, the base comprises NaOH lye (of 50% by wt concentration).

In a further embodiment of the invention the base has a iron content from 0 to 20 ppm.

In yet another embodiment of the invention, the non-solvent comprises a lower aliphatic alcohol.

In yet another embodiment of the invention, the lower aliphatic alcohol is selected from the group consisting of methanol, ethanol and isopropanol.

In yet another embodiment of the invention, the weight ratio of non-solvent to the aqueous layer is in the range of 1:1 to 2:1 preferably 1.4:1

In yet another embodiment of the invention, the iron free distilled $SO_3$ is obtained by distillation of commercial grade oleum or flash distillation of $SO_3$—liquid in a glass or glass lined distillation assembly.

DETAILED DESCRIPTION OF THE INVENTION

The present invention provides a process for the preparation of highly pure 2-Methyl-2-propene-1-sulfonic acid, sodium salt in high yield and with very low iron content by reacting distilled sulfur trioxide complexed with a Lewis base, in a halogenated solvent, removing unreacted $SO_3$ vapors, treating the mixture with liquefied isobutylene, neutralizing the reaction mixture with a base, separating the layers into a heavy organic and a lighter aqueous layer, separating the impurities from the aqueous layer by precipitation in a nonsolvent, removing the solvent to obtain the product. The distilled sulfur trioxide is substantially free from iron and is obtained preferably by distillation of commercial grade oleum or flash distillation of $SO_3$—liquid in a glass or glass lined distillation assembly.

The Lewis base is selected from dimethylformamide and dimethylacetamide and the molar ratio of the Lewis base with distilled $SO_3$ is in the range of 1.5:1 to 2.5:1, preferably 2:1. The molar ratio of isobutylene to distilled $SO_3$ is in the range of 1:1 to 1.3:1, preferably 1.15:1. The halogenated solvent is preferably ethylene dichloride and methylene chloride and is present in molar ratio of halogenated solvent to distilled $SO_3$ in the range of 5:1 to 9:1 preferably 7:1.

The base used for neutralisation comprises preferably NaOH lye (of 50% by wt concentration) and advantageously has a iron content of not more than 0 to 20 ppm. The non-solvent comprises a lower aliphatic alcohol such as methanol, ethanol, isopropanol and other lower aliphatic alcohols. The weight ratio of non-solvent to the aqueous layer is in the range of 1:1 to 2:1 preferably 1.4:1.

A most important feature of the present invention is that, iron free distilled $SO_3$ is obtained by conventional distillation of commercial grade oleum or flash distillation of $SO_3$—liquid, in a glass or glass lined distillation assembly. The iron free $SO_3$ is stored as distillate or condensate in a suitable container for using in the process.

The following examples are given by way of illustration and should not be construed to limit the scope of the present invention.

EXAMPLE 1

20 liters of 35% oleum was distilled by conventional glass distillation assembly comprising of a round bottom flask of 10 liter capacity, provided with electrical at bottom, a 25 mm diameter, 2 meter high column packed with pall rings followed by a glass condenser and a glass receiver of 8 L capacity. About 10 kg of iron free $SO_3$ was collected as distillate in the receiver.

In a glass lined jacketed and agaitated reactor of 65 L capacity, 50.85 kg Ethylene dichloride and 10.2 kg N, N-dimethylformamide, was charged. The mixture was cooled to 20° C. by circulation of chilled brine in the jacket 5.516 kg iron free distilled $SO_3$ from the glass receiver was charged slowly into this mixture under agitation. The temperature of the mixture was maintained at 20 to 25° C. during addition of iron-free distilled $SO_3$ by chilled brine circulation in jacket. After the addition was over, the vapors of unreacted $SO_3$ were sucked by applying vacuum to the system. When the vapor space was clear from the white fog, 4.44 kg isobutylene was quickly mixed with the reaction mixture. The temperature of the mixture was further raised to 42° C. It was maintained at about 42° C. for one hour. Then the mixture was cooled to 20° C., and transferred to another glass lined reactor of 125 liter capacity.

Aqueous sodium hydroxide of 20% (by wt) concentration was prepared in an HDPE container using 50% (by wt) sodium hydroxide lye having 3 ppm iron content. The reaction mixture was neutralized with 13.3 kg aqueous sodium hydroxide 20% (by wt.) to adjust the pH within 7 to 7.5. The temperature of mixture was maintained at 18 to 20° C. by circulating chilled brine in the jacket of the reactor. The mixture was digested for 1 hour 0.85 kg isobutylene was recovered from this mixture by conventional distillation. The mixture was then cooled to room temperature. Then the agitation was topped and the layers were allowed to separate.

The mixture was then cooled to room temperature. Then the agitation was stopped and the layers were allowed to separate. The heavier organic layer was separated by conventional method. Then 28 kg Methanol was charged in the reactor and the contents were cooled to 10° C. The slurry was filtered in the centrifuge. The filtrate was subjected to evaporation, concentration and distillation for removal of Methanol, water and traces of ethylene dichloride. The product obtained was further dried in conventional dryer to get 9.6 kg 2-Methyl-2-propene-1-sulfonic acid, sodium salt (94.8% yield on Isobutylene) with 99.8% purity and with 0.43 ppm iron content. The product obtained was very white in appearance and the color measured on APHA scale for 5% solution was 7.

EXAMPLE-2

The procedure followed was very similar to that elaborated in example 1 except that 11.94 kg N,N-dimethylacetamide was used instead of N,N-dimethylformamide. The product 2-Methyl-2-propene-1-sulfonic acid, sodium salt obtained as a result was very white in appearance with 99.7% purity, with 0.6 ppm iron content. The color measured on APHA scale for 5% solution was 9.

The main advantages of the present invention are:

1. This method yields the product of very superior quality with very low iron content.

2. By following this method, the side reaction sulfonation of isobutylene in vapor phase can be black coloured by products is reduced.

Thus in the methods of this invention, as compared to the usual methods, extremely high quality 2-Methyl-2-propene-1-sulfonic acid, sodium salt is obtained in high yields and of very high purity with very low iron content.

We claim:

1. A process for the preparation of highly pure 2-Methyl-2-propene-1-sulfonic acid, sodium salt in high yield and with very low iron content comprising reacting distilled sulfur trioxide complexed with a Lewis base, in a halogenated solvent, removing unreacted $SO_3$ vapors before treating the mixture with liquefied isobutylene, treating the mixture with liquefied isobutylene, neutralizing the reaction mixture with a base, separating the layers into a heavy organic and a lighter aqueous layer, precipitating the impurities from the aqueous layer by adding a non-solvent, and removing the non-solvent to obtain the product.

2. A process as claimed in claim 1 wherein the distilled sulfur trioxide is substantially free from iron.

3. A process as claimed in claim 1 wherein the Lewis base is selected from dimethylformamide or dimethylacetamide.

4. A process as claimed in claim 1 wherein the molar ratio of the Lewis base to distilled $So_3$ is in the range of 1.5:1 to 2.5:1.

5. A process as claimed in claim 4 wherein the molar ratio of the Lewis base to distilled $SO_3$ is 2:1.

6. A process as claimed in claim 1 wherein the molar ratio of isobutylene to distilled $SO_3$ is in the range of 1:1 to 1.3:1.

7. A process as claimed in claim 6 wherein the molar ratio of isobutylene to distilled $SO_3$ is 1.15:1.

8. A process as claimed in claim 1 wherein the halogenated solvent is selected from ethylene dichloride and methylene chloride.

9. A process as claimed in claim 1 wherein the molar ratio of halogenated solvent to the distilled $SO_3$ is in the range of 5:1 to 9:1.

10. A process as claimed in claim 9 wherein the molar ratio of halogenated solvent to the distilled $SO_3$ is 7:1.

11. A process as claimed in claim 1 wherein the base comprises aqueous NaOH solution with a concentration of about 50% NaOH in water.

12. A process as claimed in claim 1 wherein the base has a iron content from 0 to 20 ppm.

13. A process as claimed in claim 1 wherein the non-solvent comprises a lower aliphatic alcohol.

14. A process as claimed in claim 13 wherein the lower aliphatic alcohol is selected from the group consisting of methanol, ethanol and isopropanol.

15. A process as claimed in claim 13 wherein the weight ratio of non-solvent to the aqueous layer is in the range of 1:1 to 2:1.

16. A process as claimed in claim 13 wherein the weight ratio of non-solvent to the aqueous layer is 1.4:1.

17. A process as claimed in claim 1 wherein the iron free distilled $SO_3$ is obtained by distillation of commercial grade oleum or flash distillation of $SO_3$ —liquid in a glass or glass lined distillation assembly.

* * * * *